United States Patent [19]

Rietter et al.

[11] Patent Number: 4,977,888
[45] Date of Patent: Dec. 18, 1990

[54] LIQUID CIRCULATION SYSTEM FOR AN APPARATUS FOR DISINTEGRATING CALCULI IN THE BODY OF A LIFE FORM AND METHOD OF OPERATION

[75] Inventors: Josef Rietter, Moehrendorf; Istvan Tyukodi, Nuremberg; Reinhard Schindler, Erlangen, all of Fed. Rep. of Germany

[73] Assignee: Siemens Aktiengesellschaft, Berlin and Munich, Fed. Rep. of Germany

[21] Appl. No.: 434,506

[22] Filed: Nov. 13, 1989

Related U.S. Application Data

[63] Continuation of Ser. No. 110,834, Oct. 21, 1987, abandoned.

[30] Foreign Application Priority Data

Oct. 24, 1986 [DE] Fed. Rep. of Germany ....... 3636289

[51] Int. Cl.$^5$ ............................................. A61B 17/22
[52] U.S. Cl. .................................. 128/24 A
[58] Field of Search ........... 128/24 A, 660.03, 24 EL; 210/101

[56] References Cited

U.S. PATENT DOCUMENTS

| | | | |
|---|---|---|---|
| 4,348,280 | 9/1982 | George et al. ...................... | 210/101 |
| 4,530,358 | 7/1985 | Forssmann et al. ................ | 128/328 |
| 4,651,716 | 3/1987 | Forester et al. ................... | 128/24 A |
| 4,674,505 | 6/1987 | Pauli et al. . | |
| 4,715,375 | 12/1987 | Nowacki et al. ................. | 128/24 A |

FOREIGN PATENT DOCUMENTS

| | | | |
|---|---|---|---|
| 0225104 | 11/1986 | European Pat. Off. .......... | 128/24 A |
| 3544707 | 6/1977 | Fed. Rep. of Germany ...... | 128/328 |
| 3210919 | 7/1986 | Fed. Rep. of Germany . | |
| 2288529 | 5/1976 | France . | |
| 2063704 | 6/1981 | United Kingdom . | |

*Primary Examiner*—Kyle L. Howell
*Assistant Examiner*—John D. Zele
*Attorney, Agent, or Firm*—Hill, Van Santen, Steadman & Simpson

[57] ABSTRACT

An apparatus for disintegrating calculi in body of a life form comprises at least one shockwave generator having a chamber filled with a liquid as a coupling agent and includes a liquid circulation system having a container with a circulating pump. The liquid circulation system has a small circulation portion for normal operation and a remainder portion which includes a container for receiving the liquid and for degassifying the liquid. The small circulation portion includes a circulating pump as well as a cooler and/or a bubble separator. The portions of the system are interconnected by lines having valves so that during the step of filling, the small portion is in communication with the container, and during a step of draining of the system, the small portion and container are drained simultaneously.

14 Claims, 1 Drawing Sheet

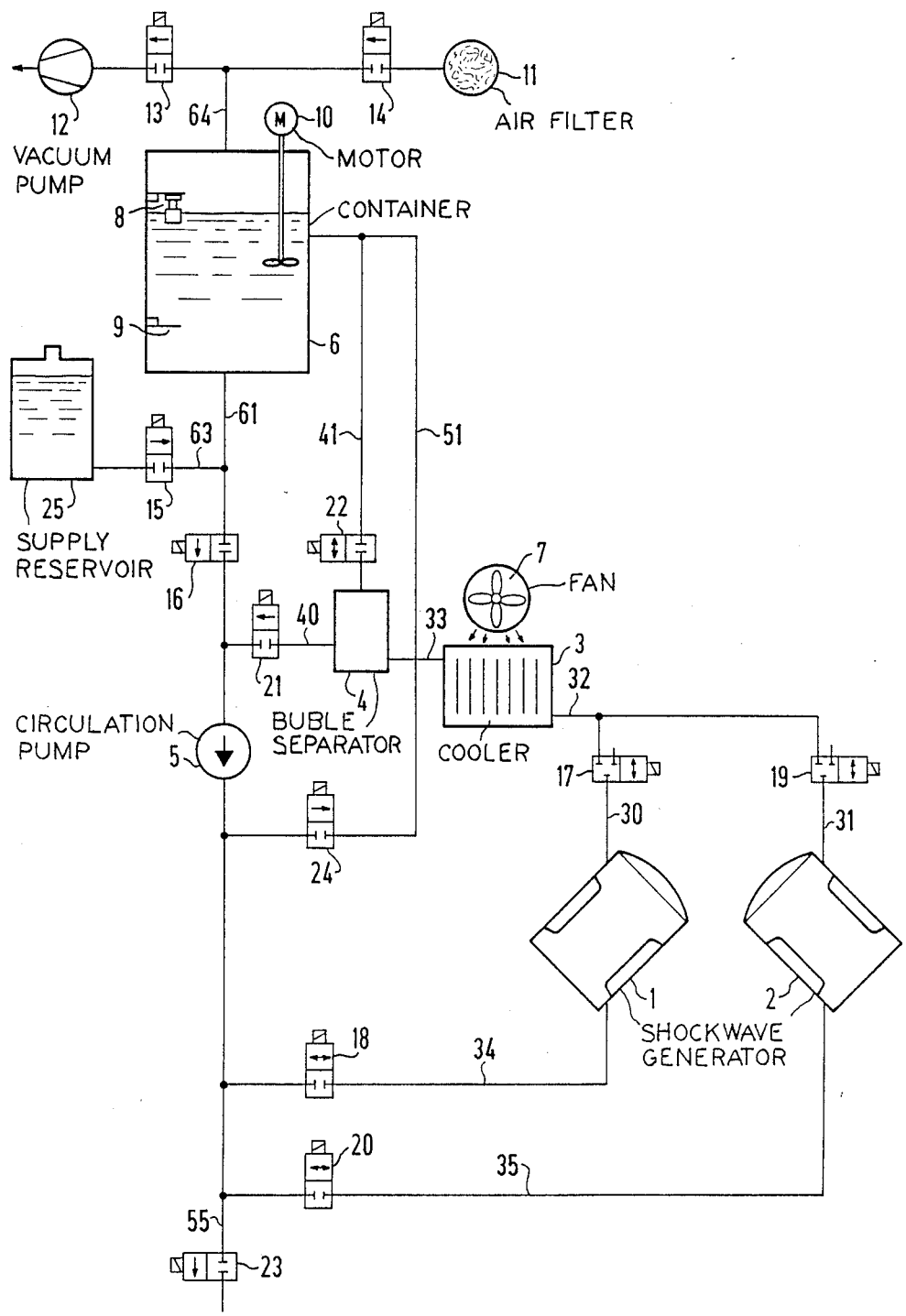

LIQUID CIRCULATION SYSTEM FOR AN APPARATUS FOR DISINTEGRATING CALCULI IN THE BODY OF A LIFE FORM AND METHOD OF OPERATION

This is a continuation of application Ser. No. 07/110,834, filed Oct. 21, 1987, now abandoned.

BACKGROUND OF THE INVENTION

The present invention is directed to an apparatus for disintegrating calculi or stones in the body of a life form. The apparatus includes at least one shockwave generator which has a chamber filled with a liquid that acts as a coupling agent and has a liquid or fluid circulation system which has a container and circulating pump for circulating the fluid through the chamber of the shockwave generator.

German Pat. No. 32 10 919 discloses an apparatus wherein a person to be examined lies in a tub filled with water. A shockwave is generated in a shockwave generator which has a spark discharge in a focussing chamber to form the shockwave. The shockwave is concentrated on the calculus situated in the patient and disintegrates it. The focussing chamber is closed by a fixed membrane and it is filled with liquid. The liquid is pumped out of a supply and compensating vessel into the focussing chamber by a circulating pump and is, again, taken therefrom in the upper region and conducted back to the supply and compensating container. However, the presence of bubbles in the liquid will cause energy losses or scattering of the shockwave. Since the supply and compensating container is always connected into the liquid circulation system, it is not guaranteed that the liquid required for the lithotripsy is adequately bubble-free.

SUMMARY OF THE INVENTION

The object of the present invention is to create an apparatus having at least one shockwave generator which has a chamber filled with liquid as a coupling agent wherein the liquid circulation guarantees that the liquid comprises only an extremely slight proportion of gas bubbles.

To accomplish these objects, the present invention provides an improvement in an apparatus for disintegrating calculi in a body life form, said apparatus including at least one shockwave generator having a chamber filled with liquid as a coupling agent, a liquid circulation system which includes a container and a circulating or circulation pump. The improvements are that the liquid circulation system includes a small circulation portion for the normal operation of the shockwave generator and a large or second circulation portion for the degassification operation. The small circulation portion includes the circulating pump, as well as a cooler and/or bubble separator. The larger second circulation portion includes the container, and the system includes valves in the various connecting lines to control the connection of the individual components into and out of the system.

Thus, the degassification process of the supplied liquid can occur separately from the small circulation of cooling fluid to each generator. An easy filling and emptying is enabled when further valves of the system make the container connectable to a source of feed water or liquid, to a vacuum pump, and to an air supply and make the liquid circulation system connectable to an out-flow or drain line. Two shockwave generators can also be used disturbance-free when they are connected in parallel to the small circulation portion by controllable valves which are present in the delivery lines and discharge lines of each of the chambers of the two shockwave generators.

The filling event for the system can occur when the container is filled first by opening the valves for the feed water and the container is connected to a vacuum pump, which is now switched on, with the simultaneous opening of the valves in the various circuits. Supply liquid, for example, water can be freed of gas bubbles when, for the degassifying of the liquid in the circulation system, the container is connected to a vacuum pump by opening a valve in a vacuum circuit and the liquid contained in the container is simultaneously circulated. The filling event of the small circulation portion, with bubble-free liquid, can occur when, for filling the shockwave generators, the valve of the air feed is, first, briefly opened and the valves of the liquid circulation system are subsequently opened and the circulating pump is switched on so that the small and second circulation portions are connected. The valves of the small circulation portion must be open for the operation of the small circulation portion. A necessary draining of the liquid, for example, when changing the shockwave generators, is achieved when, for emptying the liquid circulation system, the valves of the liquid circulation system, as well as the valve for the air supply, and a valve on a drain are opened.

Other advantages and methods will be readily apparent from the following description of the preferred embodiments, the drawing and the claims.

BRIEF DESCRIPTION OF THE DRAWING

The FIGURE is a schematic illustration of the fluid flow circuit of the present invention.

DESCRIPTION OF THE PREFERRED EMBODIMENTS

The apparatus for disintegrating calculi in the body of a life form includes two shockwave generators 1 and 2, which are similar in structure to the shockwave generators disclosed in U.S. Pat. No. 4,674,505, whose disclosure is incorporated by reference and which claims priority from German Application 33 28 051. Each of the shockwave generators includes a chamber, which is filled with a coupling agent, for example, with water. So that no scattering of the shockwaves will occur, this liquid must be as free of bubbles as possible.

The shockwave generators 1 and 2 are interconnected to the small circulation portion via lines 30, 31 and 32, with a cooler 3, which is connected by a line 33 with a bubble separator 4, which, in turn, is connected by a line 40 to a circulation or circulating pump 5, which has an outlet connected to the chamber 1 an 2 by lines 34 and 35 respectively to complete or to form a small circulation portion of the circulation system. Since the shockwave generators 1 and 2 can also be individually operated, electrically controllable valves 17–20, which enable flow in both directions are provided. As illustrated, the valve 17 is provided in an out-flow line 30 for the generator 1, while the valve 18 is in an input line 34 for the generator 1. In a similar manner, the valve 19 is in an output line 31 for the generator 2, while the input line 35 has the valve 20. In addition to these valves, the line 40, which extends from the separator 4 to an input line 61 for the circulating pump 5, has a valve 21, which is electrically controllable and only allows the fluid to pass in one direction from the separator into the line 61.

The circulation system also has a second portion which includes a tank or container 6, which is covered and has its bottom or floor connected to the intake port of the circulation pump 5 via the line 61, which has a controllable one-way valve 16. In a central region, the container is also laterally connected to a line 51, which has a controllable one-way valve 24 and extends to an output of the pump 5. In addition, a line 41, with a two-way valve 22, extends from the upper region of the bubble separator 4 to discharge into the tank or container 6. As illustrated, the line 41 is connected with the line 51 between the container 6 and the valve 24.

A supply reservoir 25 for feed water has a line 63 with a one-way electrically controllable valve 15, which line is in communication with the base or floor of the container 6. In the illustration, the line 63 is in communication with the line 61. The container 6, as mentioned before, is a closed container and has an upper region which has a line 64, which is in communication with the intake of a vacuum pump 12, which has a controllable one-way valve 13. The line 64 is also in communication with a line having a one-way valve 14 to an air filter 11, which is in communication with the ambient air or outside air.

The container 6 is provided with two float switches 8 and 9 for determining different water levels. In addition, an impeller, which may be integrated therein, is operable by a motor 10 to cause a circulation of the liquid in the container and, thus, an acceleration of the degassification.

The impeller driven by the motor 10 forms means for circulating the liquid in the container, which means can also include an additional pump, not illustrated, which is connected for causing circulation by a closed circuit pumping of the liquid in the container.

The apparatus of the present invention operates in the following manner. For filling the overall liquid circulation system, the valves 13 and 15, as well as the vacuum pump 12, are switched on so that the valves 13 and 15 are open. This switching on can be by manually actuated switch. Thus, the water is drawn from the supply reservoir 25 into the container 6 with the combination of the pressure in the supply reservoir 25 and the suction provided by the vacuum from the vacuum pump 12. When the required water level in the container 6 is reached, a float switch 8 will be actuated to create a signal to electrically close the valve 15 for the water feed line 63.

Gas bubbles, which may be potentially present, can be eliminated from the water contained in the container 6 during a degassification procedure. This occurs in that a slow circulation of the water occurs by means for circulating, which are either the basis of the operation of the impeller by the motor 10 or by the operation of the circulation pump 5, whose intake line 61 and output line 51 have their valves 16 and 24, respectively, open. However, the additional circulating pump mentioned hereinabove with regard to the means for circulating can also be actuated to cause circulation of the water in the container 6. Gas bubbles emerging from the fluid are drawn off by the vacuum pump 12. This procedure can occur, for example, on the basis of a predetermined amount of time.

After the time required for degassification has passed, the circulation pump, the motor 10, as well as the vacuum pump 12 and the valve 13, are shut off. When the liquid contained in the container 6 has been adequately degassified after a predescribed time, then the shockwave generators 1 and 2 of the small circulation portion can be simultaneously or successively filled, along with the rest of small circulation portion. To accomplish this goal, the valve 14 for the air supply is first opened so that a pressure equalization can occur in the container. It can thereby be advantageous that a slight underpressure is maintained for compensation of the flow resistance in the return lines of the small circulation portion. Subsequently, the valves 16–20 and 22 of the circulation system are opened so that the water contained in the container 6 can flow into the small circulation portion. The circulating pump 5 is switched on for promoting this flow. This can occur until bubbles no longer appear at the bubble separator 4. The circulation pump 5 can now be shut off. After a short period of time, for example, one minute, in which the water in the small circulation portion has calmed, the container 6 is then disconnected by closing the valves 16, 22 and 24 and by opening the valve 21.

By switching the circulating pump 5 on, a circulation of water will now occur only in the small circulation portion, whereas the shockwave generators 1 and 2 are situated in an inactive position outside of an operating position. Bubbles, which are still present, are collected in the bubble separator 4.

When the low water level in the container 6 has been downwardly transgressed due to the filling of the small circulation portion, then the container 6 can be filled again on the basis of the second float switch 9. The water can be degassified while the small circulation portion is operating by closing the valve 14, and then by applying a vacuum to the container 6 and creating a circulation of the fluid in the container by operating the motor 10.

For operation of the lithotriptor, at least one of the two shockwave generators 1 and 2 is brought from its inactive position to an operating position. Assuming that it is the shockwave generator 1, then the shockwave generator 2 is isolated from the small circulating portion by closing the valves 19 and 20 while the valves 17 and 18 remain open to maintain the shockwave generator 1 in the system. Thus, the fluid will now flow only through the shockwave generator 1. The shockwave generator 1 is then cooled by a constant liquid circulation during operation. To promote the cooling effect, a ventilator or fan 7 for the air circulation can be associated with the cooler 3. If the generator 2 is selected instead of the generator 1, the valves 19 and 20 are opened, while the valves 17 and 18 are closed.

After conclusion of the treatment with the shockwave generator, these are again brought into their inactive position and all the valves 17, 18, 19 and 20 are in the opened position so that water can, again, move through each of the generators.

The liquid in the shockwave generators 1 and 2 and in the rest of the circulation portion can be automatically prepared from time-to-time at prescribed intervals. Previously, the degassification procedure in the container 6 is carried out simultaneously during the operation of the small circulation portion. To this end, the valve 13 is again opened and a vacuum pump 12 is switched on and the liquid in the container 6 is circulated. This can occur with the impeller operated by the motor 10 or with the additional circulating pump (not shown). When the degassification procedure is concluded, the abovedescribed pressure equalization, again, is produced. Subsequently, the valve 22 is opened so that the air collected in the bubble separator 4 will escape into the container 6. Simultaneously, the small circulation portion is refilled with the degassified water in the container 6 so that it is always guaranteed that the coupling liquid in the shockwave generators 1 and 2 is free of bubbles.

When, for example, either one of the shockwave generators 1 and 2, or both, are to be replaced, then the water in the liquid circulation system can be drained off. For emptying the liquid circulation system, each of the valves 14, 16–22, as well as a valve 23, which is in a drain line 55, are opened so that the water contained in the liquid circulation system can flow out the drain. Air can enter the system via the air supply so that a vacuum which may potentially occur is prevented.

Although various minor modifications may be suggested by those versed in the art, it should be understood that we wish to embody within the scope of the patent granted hereon all such modifications as reasonably and properly come within the scope of our contribution to the art.

We claim:

1. In an apparatus for disintegrating calculi in the body of a life form, said apparatus comprising a shockwave generator having a chamber filled with a liquid coupling agent, and a liquid circulation system which is connected to the chamber and has a container and a circulation pump, the improvements comprising the liquid circulation system being formed by a small circulating portion for circulating a liquid through the chamber and a second circulation portion for a degassification operation, said small circulation portion connected to the chamber of the shockwave generator including the circulation pump, first and second lines extending between said chamber and circulation pump, and a cooler and a bubble separator being positioned on one of said first and second lines, said second circulation portion including the container, said system including liquid connecting lines extending between the container and said small circulation portion and said system having valves for controlling flow in the liquid connecting lines extending between the second circulation portion and the small circulation portion to enable control of the flow of liquids between the second and small portions.

2. In an apparatus according to claim 1, wherein the apparatus further includes a second shockwave generator connected in parallel with the first mentioned generator, each of said shockwave generators having first and second lines with control valves to enable selective connection of the particular generator to the small circulation portion.

3. In an apparatus according to claim 1, wherein the circulation system includes a drain line being connected to said small circulation portion and having a valve, said container is a closed container and the circulation system includes a feed water reservoir, a feed water line having a valve connecting the container to said feed water reservoir, a vacuum pump having a line with a valve for applying a vacuum to the closed container and an air supply line with a valve for supplying ambient air to said closed container.

4. In an apparatus according to claim 3, wherein the apparatus further includes a second shockwave generator connected in parallel with the first-mentioned generator, each of said shockwave generators having first and second lines with control valves so that they can be coupled to the small circulation portion.

5. A method of liquid circulation in an apparatus for disintegrating calculi in the body of a life form, said apparatus having a liquid circulation system and at least one shockwave generator having a chamber being filled with said liquid as a coupling agent and being connected to said liquid circulation system, said liquid circulation system including a feed water reservoir and a closed container connected by a line with a valve to the feed water reservoir, said container having at least one line having a valve extending to a vacuum pump, means for connecting a top of the closed container to ambient air, said means including a line with a valve, the method including filling said container by the steps of opening the valve in the line from the feed water reservoir and actuating the vacuum pump with the valve in the line to the vacuum pump being opened to apply a suction above the liquid in said container.

6. A method according to claim 5, which includes determining a liquid level in the container and, when the liquid level reaches a predetermined amount, closing the valve on the line to the feed water reservoir.

7. A method according to claim 5, which includes, subsequent to filling the container, degassifying the liquid in the container by continuing to apply a vacuum to the upper portion of the container, while slowly circulating the liquid in the container to allow the bubbles in the liquid to be removed.

8. In a method according to claim 7, wherein the system includes a small circulation portion including a circulation pump, a cooler, and bubble separator, said small portion being connected by lines with valves to the container of the liquid circulation system, said method comprising the steps of filling the small circulation portion by opening the valve in the line extending to the ambient air for a brief moment to equalize the pressure in the container, then opening the valves in the lines connecting the container to the small circulation portion while operating the circulation pump for circulating the liquid into the small circulation portion.

9. A method according to claim 8, which includes, subsequent to filling said small circulation portion, isolating the small circulation portion from the container by closing the valves in the lines extending therebetween so that liquid is circulated by the circulation pump from each chamber to the cooler, then the bubble separator, then the pump and back to the chamber.

10. A method according to claim 8, which subsequently includes draining the entire system, including opening a valve in a drain line for the circulation system and opening all of the valves in the lines between the small circulation portion and the container of the circulation system, while opening the valve to vent the container to the ambient air.

11. A method for operating a circulation system in an apparatus for disintegrating calculi, said apparatus having at least one shockwave generator each having a chamber filled with a liquid as a coupling agent, said circulation system including a cooler, a bubble separator, and a pump connected as a small circulation portion of the circulation system to each chamber, said system including a container of liquid and lines connecting the small portion to said container of liquid, said container having means for circulating a liquid in the container, said container being a closed container having a top with at least one line extending from the top in communication with a valve for an intake of a vacuum pump and said top having a line with a valve in communication with ambient air, said method comprising first degassifying liquid in the container by closing the valve to ambient air and opening the valve to the vacuum pump, operating the vacuum pump to provide a vacuum in the container, and actuating said means for circulating the liquid in the container to facilitate the escape of bubbles from the liquid.

12. A method according to claim 11, which includes, subsequent to degassifying the liquid in the container, stopping the vacuum pump and closing the valve in the line to the vacuum pump, opening the valve to ambient air to briefly equalize the pressure in the container, then opening the lines connecting the small circulation portion to the container and actuating the pump in the small circulation portion to draw liquid from the container and into the small circulation portion, then, after filling the small portion, isolating the small portion by closing the valves in the line extending between the small circulation portion and the container.

13. In a method according to claim 12, which includes, subsequent to filling the small portion and isolating it, operating the pump to circulate the liquid in the small portion and, simultaneously replacing liquid in the container by energizing the vacuum pump, opening the valve of the intake to the vacuum pump while closing the valve to the ambient air, opening a valve on a water supply reservoir to introduce liquid into the container, subsequent to filling the container, closing the valve on the line from the water reservoir and continuing to operate the vacuum pump while actuating the means for circulating the liquid in the container.

14. In a method according to claim 12, which further includes the step of draining the liquids from the small portion and the container by opening a valve on a drain line and opening the valves in the lines connecting the small portion to the container and the valves in the small portion, and opening the valve in the line extending to the atmosphere so that liquid in the container and small portion can drain from the system.

* * * * *